United States Patent
Choi et al.

(10) Patent No.: US 10,332,751 B2
(45) Date of Patent: Jun. 25, 2019

(54) MONOMER, ORGANIC LAYER COMPOSITION, ORGANIC LAYER, AND METHOD OF FORMING PATTERNS

(71) Applicant: SAMSUNG SDI CO., LTD., Yongin-si, Gyeonggi-do (KR)

(72) Inventors: Yoo-Jeong Choi, Suwon-si (KR);
Yun-Jun Kim, Suwon-si (KR);
Yu-Shin Park, Suwon-si (KR);
You-Jung Park, Suwon-si (KR);
Hyun-Ji Song, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 0 days.

(21) Appl. No.: 14/979,634

(22) Filed: Dec. 28, 2015

(65) Prior Publication Data

US 2016/0237306 A1   Aug. 18, 2016

(30) Foreign Application Priority Data

Feb. 17, 2015   (KR) .................. 10-2015-0024473

(51) Int. Cl.
| | | |
|---|---|---|
| *C07D 215/14* | (2006.01) | |
| *C07D 311/58* | (2006.01) | |
| *H01L 21/311* | (2006.01) | |
| *C07C 39/225* | (2006.01) | |
| *C08G 61/02* | (2006.01) | |
| *C08G 61/12* | (2006.01) | |
| *C09D 165/00* | (2006.01) | |
| *H01L 21/027* | (2006.01) | |

(52) U.S. Cl.
CPC ...... *H01L 21/31116* (2013.01); *C07C 39/225* (2013.01); *C07D 215/14* (2013.01); *C07D 311/58* (2013.01); *C08G 61/02* (2013.01); *C08G 61/122* (2013.01); *C09D 165/00* (2013.01); *H01L 21/0271* (2013.01); *H01L 21/31144* (2013.01); *C08G 2261/135* (2013.01); *C08G 2261/1422* (2013.01); *C08G 2261/314* (2013.01); *C08G 2261/3241* (2013.01); *C08G 2261/3242* (2013.01); *C08G 2261/3424* (2013.01); *C08G 2261/76* (2013.01); *H01L 21/31138* (2013.01)

(58) Field of Classification Search
None
See application file for complete search history.

(56) References Cited

U.S. PATENT DOCUMENTS

| | | | | |
|---|---|---|---|---|
| 9,556,094 | B2 * | 1/2017 | Kim .................. | C07C 39/14 |
| 2014/0186777 | A1 * | 7/2014 | Lee .................. | C07C 33/26 |
| | | | | 430/325 |
| 2015/0001178 | A1 | 1/2015 | Song et al. | |
| 2015/0274622 | A1 * | 10/2015 | Kim .................. | C07C 39/14 |
| | | | | 216/49 |

FOREIGN PATENT DOCUMENTS

| | | | | |
|---|---|---|---|---|
| CN | 102876263 | A | 1/2013 | |
| CN | 103896736 | A | 7/2014 | |
| CN | 103910610 | A | 7/2014 | |
| CN | 103959170 | A | 7/2014 | |
| CN | 104024940 | A | 9/2014 | |
| JP | 2014-029435 | A | 2/2014 | |
| KR | 10-2013-0078745 | A | 7/2013 | |
| KR | 10-2014-0083695 | A | 7/2014 | |
| KR | 10-2014-0085122 | A | 7/2014 | |
| KR | 10-2014-0085124 | A | 7/2014 | |
| KR | 10-2014-0086735 | A | 7/2014 | |
| KR | 10-1413071 | B1 | 7/2014 | |
| KR | 2014083695 | * | 7/2014 | ............. C07C 39/12 |
| KR | 10-2014-0104791 | A | 8/2014 | |
| KR | 10-2015-0002929 | A | 1/2015 | |
| KR | 10-2015-0002931 | A | 1/2015 | |
| WO | WO 2014-065500 | A | 5/2014 | |
| WO | WO 2014-104496 | A | 7/2014 | |
| WO | WO 2014/104496 | A1 * | 7/2014 | |

OTHER PUBLICATIONS

Zuidema, et al., "Synthetic Communications: An International Journal for Rapid Communication of Synthetic Organic Chemistry," (2011). 41, pp. 2927-2931.
Chinese Office Action, dated Nov. 16, 2017, in connection with the corresponding Chinese Patent Application No. 201511020947.X.
Jinhua J. Song et al, N-Heterocyclic Carbene Catalyzed Trifluoromethylation of Carbonyl Compounds, American Chemical Society (2005), Organic Letters, 2005, vol. 7, No. 11, 2193-2196.
Marcin Stepien et al, Steric Control in the Synthesis of p-Benziporphyrins. Formation of a Doubly N-Confused Benzihexaphyrin Macrocycle, American Chemical Society (2009), Organic Letters, 2009, vol. 11, No. 17, 3930-3933.
Xuejiao Jia et al., Mg-Prompted Polyfluoroarene C—H Functionalization: Formal Synthesis of Transfluthrin, Fenfluthrin and Tefluthrin, American Chemical Society (2015), Oct. 9, 2015.
Provisional double patenting rejection over claims of the above-identified application; USPTO Office action dated May 11, 2018, in U.S. Appl. No. 14/258,489.

* cited by examiner

*Primary Examiner* — Noble E Jarrell

(74) *Attorney, Agent, or Firm* — Lee & Morse, P.C.

(57) ABSTRACT

A monomer, an organic layer composition including the monomer, an organic layer, and a method of forming patterns, the monomer being represented by Chemical Formula 1:

[Chemical Formula 1]

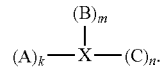

15 Claims, No Drawings

MONOMER, ORGANIC LAYER COMPOSITION, ORGANIC LAYER, AND METHOD OF FORMING PATTERNS

CROSS-REFERENCE TO RELATED APPLICATION

Korean Patent Application No. 10-2015-0024473, filed on Feb. 17, 2015, in the Korean Intellectual Property Office, and entitled: "Monomer, Organic Layer Composition, Organic Layer, and Method of Forming Patterns," is incorporated by reference herein in its entirety.

BACKGROUND

1. Field

Embodiments relate to a monomer, an organic layer composition including the monomer, an organic layer, and a method of forming patterns.

2. Description of the Related Art

A high integration design in accordance with down-sizing (miniaturization) and complexity of an electronic device has accelerated development of a more advanced material and its related process, and accordingly, lithography using a conventional photoresist may utilize new patterning materials and techniques. In a patterning process, an organic layer (called a hardmask layer) may be formed as a hard interlayer to transfer the fine pattern of the photoresist down to a sufficient depth on a substrate without a collapse. The hardmask layer may play a role of an interlayer transferring the fine pattern of the photoresist to a material layer through a selective etching process and thus may exhibit etch resistance so that it may endure multi-etching processes.

SUMMARY

Embodiments are directed to a monomer, an organic layer composition including the monomer, an organic layer, and a method of forming patterns The embodiments may be realized by providing a monomer represented by Chemical Formula 1:

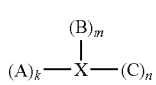

[Chemical Formula 1]

wherein, in Chemical Formula 1, X is a substituted or unsubstituted aromatic ring group, A, B, and C are each independently a group represented by Chemical Formula 2, k, m, and n are independently 0 or 1, a sum of k, m, and n being 2 or 3, when k=m=1, A and B are different groups from each other, when k=n=1, A and C are different groups from each other, and when m=n=1, B and C are different groups from each other, and when k=m=n=1, at least two of A, B, and C are different groups from each other,

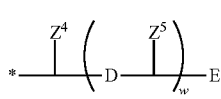

[Chemical Formula 2]

wherein, in Chemical Formula 2, D and E are each independently a substituted or unsubstituted aromatic ring group, a substituted or unsubstituted heteroaromatic ring group, or a combination thereof, $Z^4$ and $Z^5$ are each independently a hydroxy group, a thionyl group, a thiol group, a cyano group, a substituted or unsubstituted amino group, a halogen atom, a halogen-containing group, or a combination thereof, w is 0 or 1, and * is a linking point.

The monomer may be represented by one of Chemical Formulae 1-1 and 1-2:

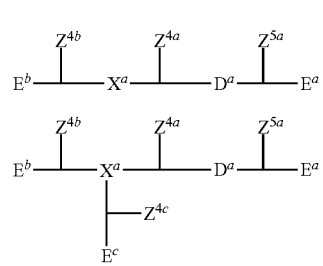

[Chemical Formula 1-1]

[Chemical Formula 1-2]

wherein, in Chemical Formulae 1-1 and 1-2, $X^a$ may be a substituted or unsubstituted aromatic ring group, $D^a$, $E^a$, $E^b$, and $E^c$ may each independently be a substituted or unsubstituted aromatic ring group, a substituted or unsubstituted heteroaromatic ring group, or a combination thereof, and $Z^{4a}$, $Z^{4b}$, $Z^{4c}$, and $Z^{5a}$ may each independently be a hydroxy group, a thionyl group, a thiol group, a cyano group, a substituted or unsubstituted amino group, a halogen atom, a halogen-containing group, or a combination thereof.

In Chemical Formula 1-1, at least one of $D^a$, $E^a$, and $E^b$ may be a substituted or unsubstituted polycyclic aromatic ring group, a substituted or unsubstituted polycyclic heteroaromatic ring group, or a combination thereof, or in Chemical Formula 1-1, $X^a$ may be a substituted or unsubstituted polycyclic aromatic ring group, and in Chemical Formula 1-2, at least one of $D^a$, $E^a$, $E^b$, and $E^c$ may be a substituted or unsubstituted polycyclic aromatic ring group, a substituted or unsubstituted polycyclic heteroaromatic ring group, or a combination thereof, or in Chemical Formula 1-2, $X^a$ may be a substituted or unsubstituted polycyclic aromatic ring group.

In Chemical Formulae 1-1 and 1-2, $D^a$, $E^a$, $E^b$, and $E^c$ may each independently be a substituted or unsubstituted group of one of the following compounds:

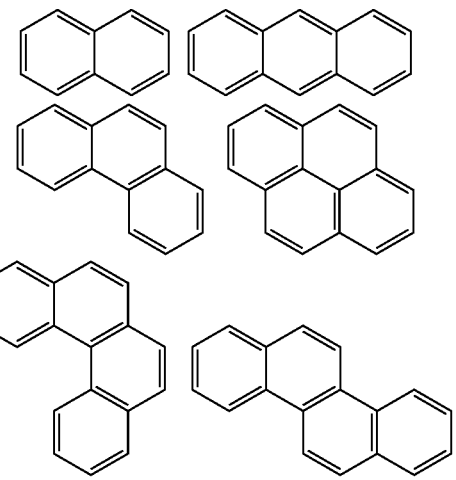

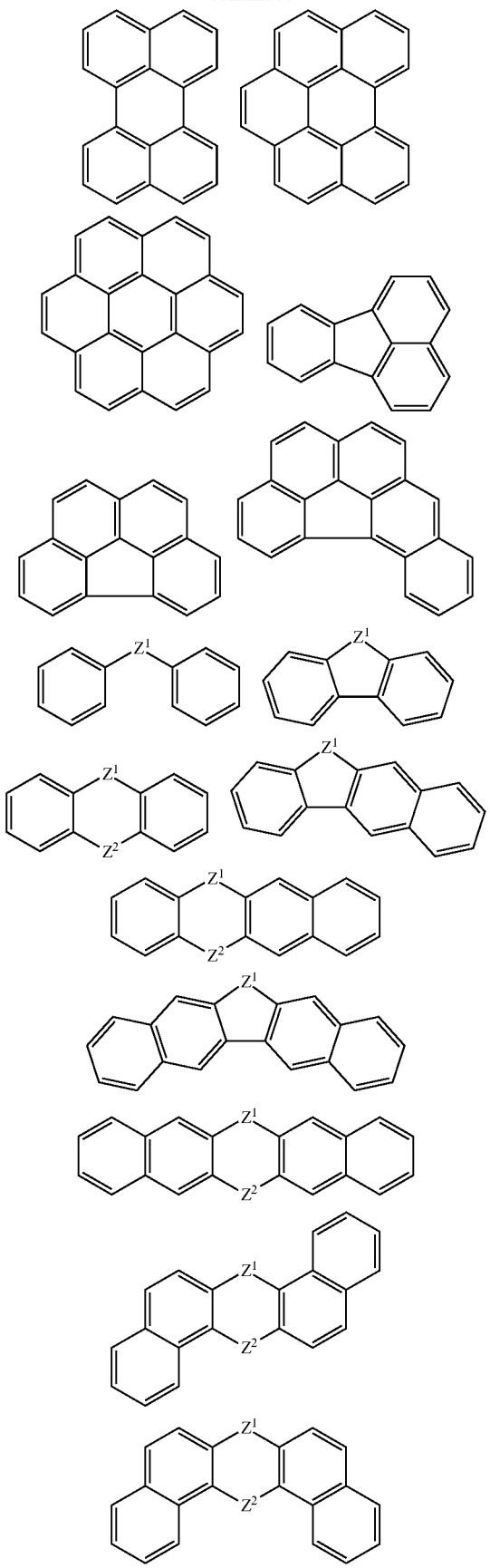

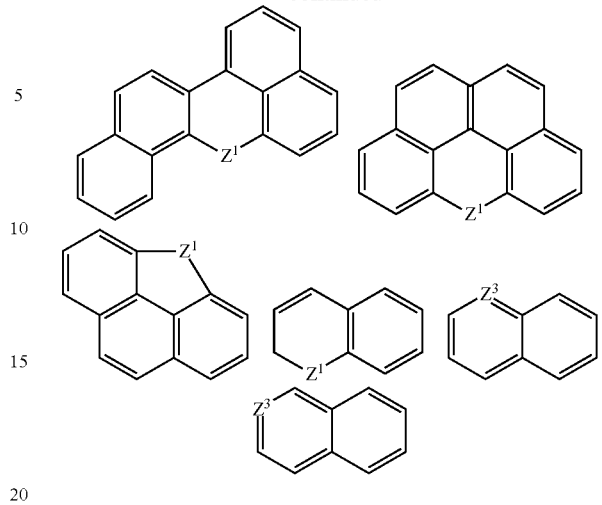

wherein, in the above compounds, $Z^1$ and $Z^2$ may each independently be a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR, oxygen (O), sulfur (S), or a combination thereof, $Z^3$ may be nitrogen (N), CR, or a combination thereof, and R may be hydrogen, a substituted or unsubstituted C1 to C10 alkyl group, a halogen atom, a halogen-containing group, or a combination thereof.

In Chemical Formulae 1-1 and 1-2, $X^a$ may be a substituted or unsubstituted group of one of the following compounds:

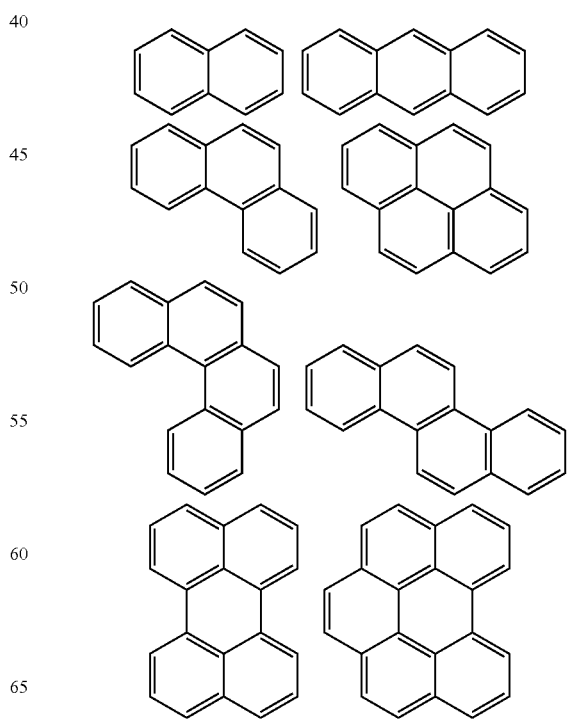

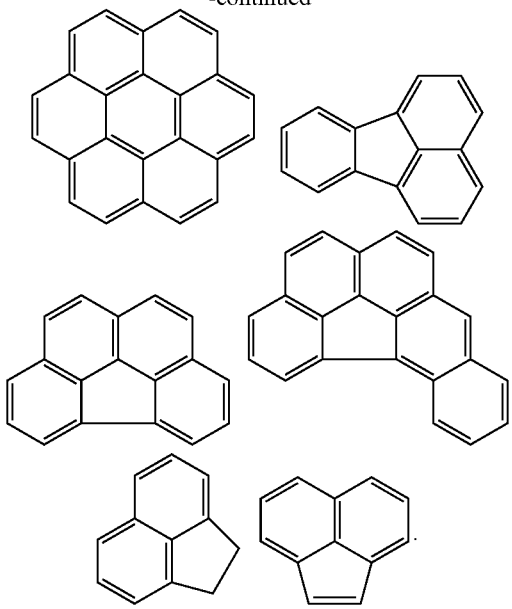

In Chemical Formula 1-1, at least one of $X^a$, $D^a$, $E^a$, and $E^b$ may be a group that includes a hydroxy group, and in Chemical Formula 1-2, at least one of $X^a$, $D^a$, $E^a$, $E^b$, and $E^c$ may be a group that includes a hydroxy group.

The monomer may have a molecular weight of about 800 to about 5,000.

The embodiments may be realized by providing an organic layer composition including a solvent; and a monomer represented by Chemical Formula 1,

[Chemical Formula 1]

wherein, in Chemical Formula 1, X is a substituted or unsubstituted aromatic ring group, A, B, and C are each independently a group represented by Chemical Formula 2, k, m, and n are each independently 0 or 1, a sum of k, m, and n being 2 or 3, when k=m=1, A and B are different groups from each other, when k=n=1, A and C are different groups from each other, and when m=n=1, B and C are different groups from each other, and when k=m=n=1, at least two of A, B, and C are different groups from each other,

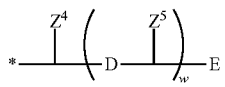

[Chemical Formula 2]

wherein, in Chemical Formula 2, D and E are each independently a substituted or unsubstituted aromatic ring group, a substituted or unsubstituted heteroaromatic ring group, or a combination thereof, $Z^4$ and $Z^5$ are each independently a hydroxy group, a thionyl group, a thiol group, a cyano group, a substituted or unsubstituted amino group, a halogen atom, a halogen-containing group, or a combination thereof, w is 0 or 1, and * is a linking point.

The monomer may be represented by one of Chemical Formulae 1-1 and 1-2:

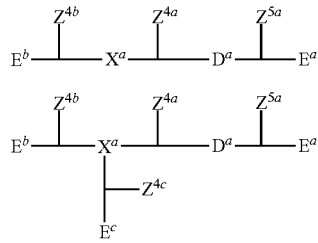

[Chemical Formula 1-1]

[Chemical Formula 1-2]

wherein, in Chemical Formulae 1-1 and 1-2, $X^a$ may be a substituted or unsubstituted aromatic ring group, $D^a$, $E^a$, $E^b$, and $E^c$ may each independently be a substituted or unsubstituted aromatic ring group, a substituted or unsubstituted heteroaromatic ring group, or a combination thereof, $Z^{4a}$, $Z^{4b}$, $Z^{4c}$, and $Z^{5a}$ may each independently be a hydroxy group, a thionyl group, a thiol group, a cyano group, a substituted or unsubstituted amino group, a halogen atom, a halogen-containing group, or a combination thereof.

In Chemical Formula 1-1, at least one of $D^a$, $E^a$, and $E^b$ may be a substituted or unsubstituted polycyclic aromatic ring group, a substituted or unsubstituted polycyclic heteroaromatic ring group, or a combination thereof, or in Chemical Formula 1-1, $X^a$ may be a substituted or unsubstituted polycyclic aromatic ring group, and in Chemical Formula 1-2, at least one of $D^a$, $E^a$, $E^b$, and $E^c$ may be a substituted or unsubstituted polycyclic aromatic ring group, a substituted or unsubstituted polycyclic heteroaromatic ring group, or a combination thereof, or in Chemical Formula 1-2, $X^a$ may be a substituted or unsubstituted polycyclic aromatic ring group.

In Chemical Formulae 1-1 and 1-2, $D^a$, $E^a$, $E^b$, and $E^c$ may each independently be a substituted or unsubstituted group of one of the following compounds:

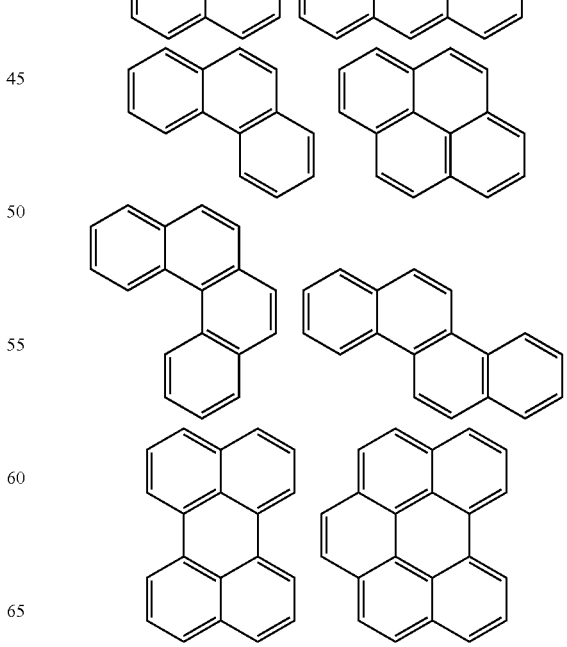

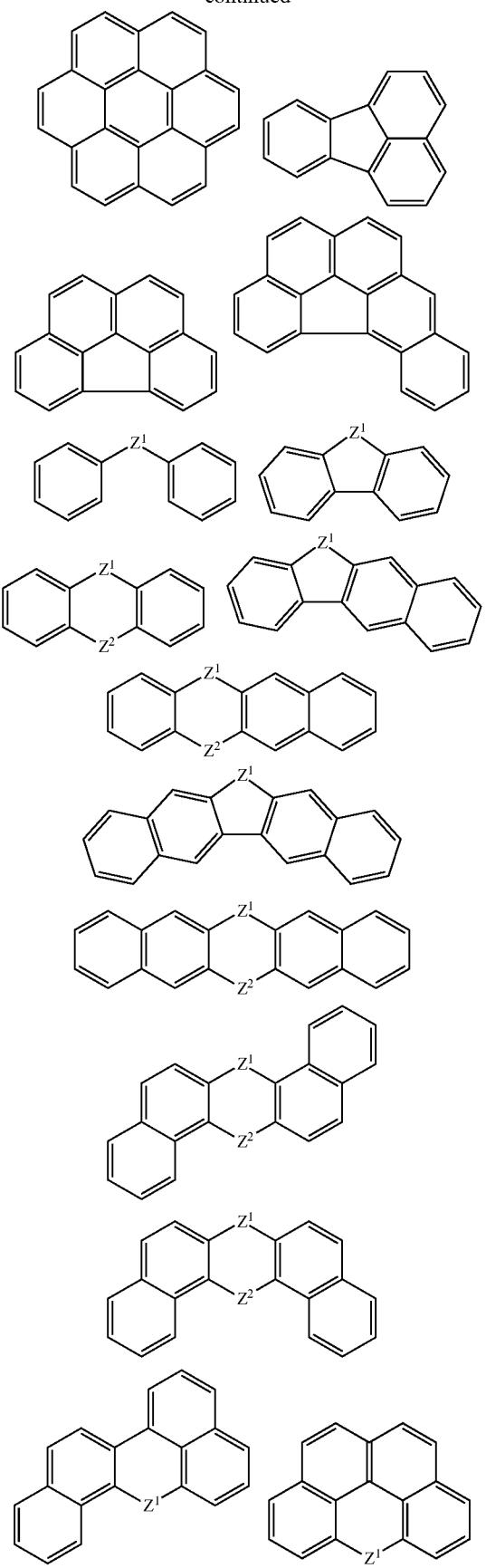

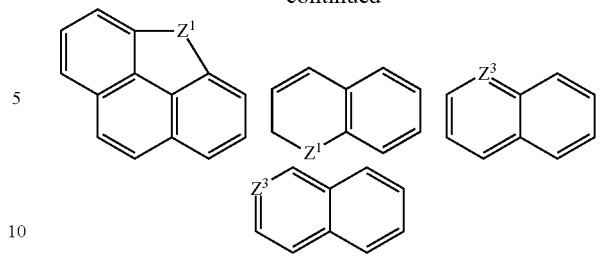

wherein, in the above compounds, $Z^1$ and $Z^2$ may each independently be a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR, oxygen (O), sulfur (S), or a combination thereof, $Z^3$ may be nitrogen (N), CR, or a combination thereof, and R may be hydrogen, a substituted or unsubstituted C1 to C10 alkyl group, a halogen atom, a halogen-containing group, or a combination thereof.

In Chemical Formulae 1-1 and 1-2, $X^a$ may be a substituted or unsubstituted group of one of the following compounds:

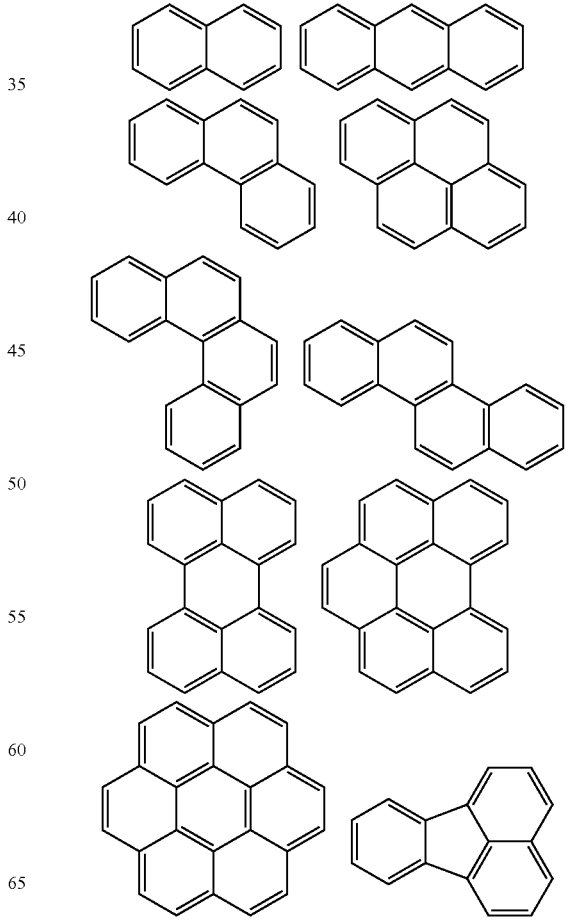

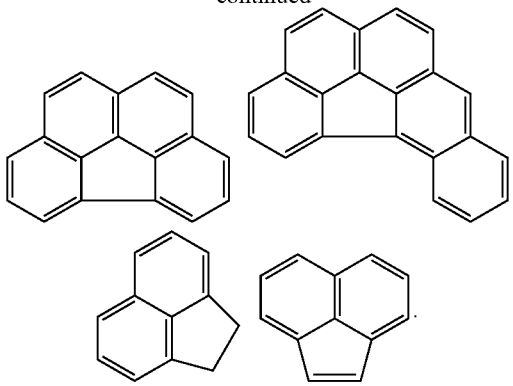

In Chemical Formula 1-1, at least one of $X^a$, $D^a$, $E^a$, and $E^b$ may be a group that includes a hydroxy group, and in Chemical Formula 1-2, at least one of $X^a$, $D^a$, $E^a$, $E^b$, and $E^c$ may be a group that includes a hydroxy group.

The monomer may have a molecular weight of about 800 to about 5000.

The embodiments may be realized by providing an organic layer formed by curing the organic layer composition according to an embodiment.

The organic layer may include a hardmask layer.

The embodiments may be realized by providing a method of forming patterns, the method including providing a material layer on a substrate, applying the organic layer composition according to an embodiment on the material layer, heat-treating the organic layer composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

Applying the organic layer composition may include performing a spin-on coating method.

DETAILED DESCRIPTION

Example embodiments will now be described more fully hereinafter; however, they may be embodied in different forms and should not be construed as limited to the embodiments set forth herein. Rather, these embodiments are provided so that this disclosure will be thorough and complete, and will fully convey exemplary implementations to those skilled in the art.

It will also be understood that when a layer or element is referred to as being "on" another layer or element, it can be directly on the other layer or element, or intervening layers may also be present.

As used herein, when a definition is not otherwise provided, the term 'substituted' may refer to one substituted with a substituent selected from a halogen atom (F, Br, Cl, or I), a hydroxy group, an alkoxy group, a nitro group, a cyano group, an amino group, an azido group, an amidino group, a hydrazino group, a hydrazono group, a carbonyl group, carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C30 heterocycloalkyl group, and a combination thereof, instead of hydrogen of a compound.

As used herein, when a definition is not otherwise provided, the term 'hetero' refers to one including 1 to 3 heteroatoms selected from B, N, O, S, and P.

Hereinafter, a monomer according to one embodiment is described.

A monomer according to one embodiment may be represented by Chemical Formula 1.

[Chemical Formula 1]

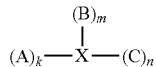

In Chemical Formula 1,

X may be or may include, e.g., a substituted or unsubstituted aromatic ring group.

A, B, and C may each independently be, e.g., a group represented by Chemical Formula 2.

k, m, and n may each independently be 0 or 1, and a sum of k, m, and n may be 2 or 3.

When k, m, or n are 0, X are respectively substituted with hydrogen instead of A, B or C. For example, a hydrogen atom may take the place of A, B, or C in Chemical Formula 1.

[Chemical Formula 2]

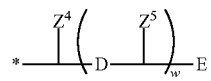

In Chemical Formula 2,

D and E may each independently be or include, e.g., a substituted or unsubstituted aromatic ring group, a substituted or unsubstituted heteroaromatic ring group, or a combination thereof.

$Z^4$ and $Z^5$ may each independently be or include, e.g., a hydroxy group, a thionyl group, a thiol group, a cyano group, a substituted or unsubstituted amino group, a halogen atom, a halogen-containing group, or a combination thereof.

w may be 0 or 1.

* is a linking point.

The monomer represented by Chemical Formula 1 may have a structure in which two or three substituents are linked to a core of an aromatic ring group, and the substituents may include, e.g., an aromatic ring group, a heteroaromatic ring group, or a combination thereof.

In Chemical Formula 1, when k=m=1, A and B may be different groups from each other, when k=n=1, A and C may be different groups from each other, and when m=n=1, B and C may be different groups from each other.

For example, when the monomer has a structure where two substituents are linked to a core, the two substituents may be different groups. Thus, the monomer may have an asymmetric structure about the core.

In Chemical Formula 1, when k=m=n=1, at least two of three substituents (A, B and C) linked to the core X may be different from each other.

For example, when the monomer has a structure in which three substituents are linked to a core, at least two substituents of the three substituents may be different. Thus, the monomer may have an asymmetric structure about the core.

For example, the monomer may have a structure in which substituents are asymmetrically or irregularly linked to a core and thus may exhibit improved solubility, as compared with a monomer having a symmetrical or regular structure. Accordingly, a solution including the monomer may be less likely to generate a precipitate, and resultantly, gap-fill characteristics and planarization characteristics may be improved.

In an implementation, when the monomer has two substituents on the core, the monomer may be represented by Chemical Formula 1-1, and when the monomer has three substituents on the core, the monomer may be represented by Chemical Formula 1-2.

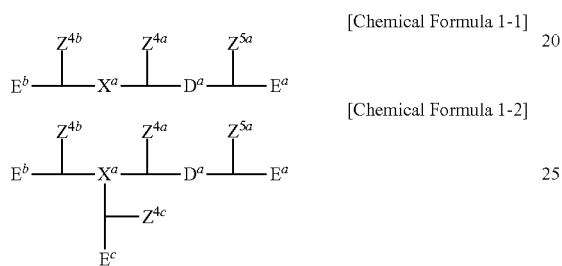

[Chemical Formula 1-1]

[Chemical Formula 1-2]

In Chemical Formulae 1-1 and 1-2, $X^a$ may be or may include, e.g., a substituted or unsubstituted aromatic ring group.

$D^a$, $E^a$, $E^b$, and $E^c$ may each independently be or include, e.g., a substituted or unsubstituted aromatic ring group, a substituted or unsubstituted heteroaromatic ring group, or a combination thereof.

$Z^{4a}$, $Z^{4b}$, $Z^{4c}$, and and $Z^{5a}$ may each independently be or include, e.g., a hydroxy group, a thionyl group, a thiol group, a cyano group, a substituted or unsubstituted amino group, a halogen atom, a halogen-containing group, or a combination thereof.

The monomer may have rigid characteristics by including at least one polycyclic cyclic group in the core or the substituent.

In an implementation, at least one of $D^a$, $E^a$, and $E^b$ in Chemical Formula 1-1 may be or may include, e.g., a substituted or unsubstituted polycyclic aromatic ring group, a substituted or unsubstituted polycyclic heteroaromatic ring group, or a combination thereof, and/or $X^a$ in Chemical Formula 1-1 may be or may include, e.g., a substituted or unsubstituted polycyclic aromatic ring group.

For example, in Chemical Formula 1-2, at least one of $D^a$, $E^a$, $E^b$, and $E^c$ may be or may include, e.g., a substituted or unsubstituted polycyclic aromatic ring group, a substituted or unsubstituted polycyclic hetero aromatic ring group, or a combination thereof, and/or in Chemical Formula 1-2, the $X^a$ may be or may include, e.g., a substituted or unsubstituted polycyclic aromatic ring group.

In an implementation, in Chemical Formulae 1-1 and 1-2, $D^a$, $E^a$, $E^b$, and $E^c$ may each independently be or include a substituted or unsubstituted group of the following compounds, e.g., a cyclic group of the following compounds or a cyclic group of the following compounds where at least one hydrogen is replaced by a substituent.

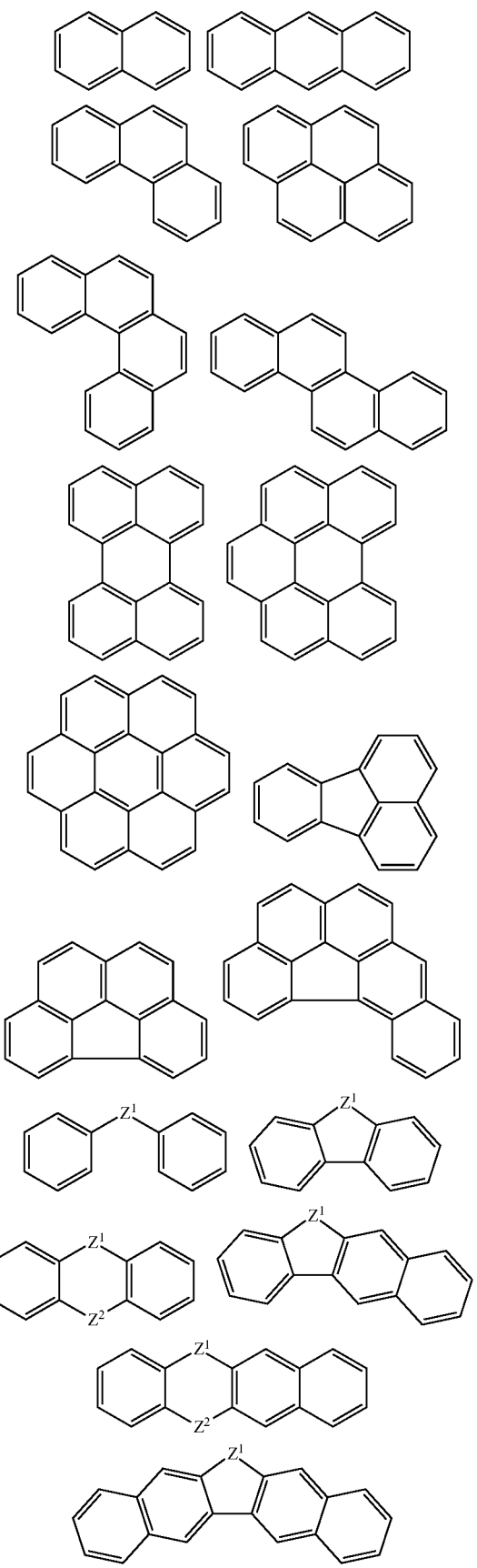

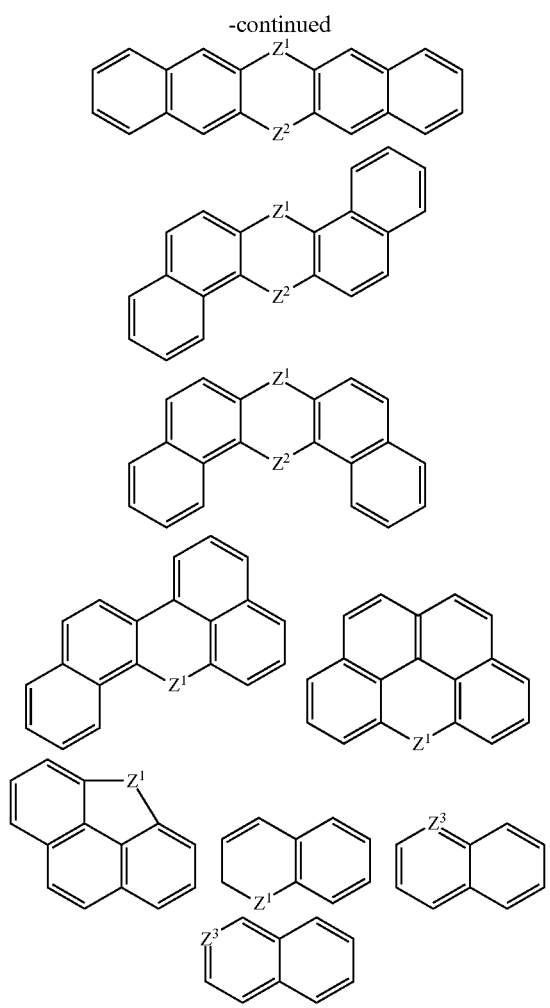

In the above compounds, $Z^1$ and $Z^2$ may each independently be or include, e.g., a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR, oxygen (O), sulfur (S), or a combination thereof.

$Z^3$ may be, e.g., nitrogen (N), CR, or a combination thereof.

R may be or may include, e.g., hydrogen, a substituted or unsubstituted C1 to C10 alkyl group, a halogen atom, a halogen-containing group, or a combination thereof.

In an implementation, in Chemical Formulae 1-1 and 1-2, $X^a$ may be a substituted or unsubstituted group of one of the following compounds, e.g., a cyclic group of the following compounds or a cyclic group of the following compounds where at least one hydrogen is replaced by a substituent.

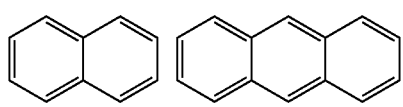

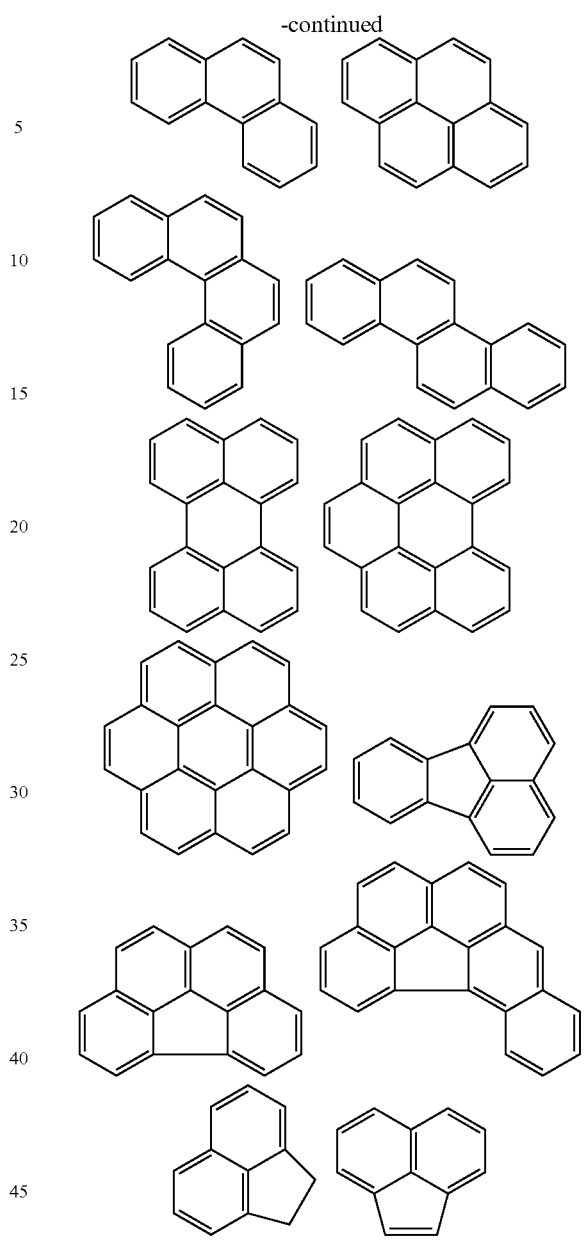

The groups of the above compounds may be linked at a suitable position.

In the monomer, the aromatic ring group or the heteroaromatic ring group positioned at a substituent may be either substituted or unsubstituted, e.g., may be substituted with a hydroxy group. For example, in Chemical Formula 1-1, at least one of $X^a$, $D^a$, $E^a$ and $E^b$ may be a group that includes a hydroxy group (e.g., may be a group substituted with a hydroxy group), and in Chemical Formula 1-2, at least one of $X^a$, $D^a$, $E^a$, $E^b$, and $E^c$ may be a group that includes a hydroxy group (e.g., may be a group substituted with a hydroxy group). Herein, the substituting hydroxy group may be included in a suitable number and/or at a suitable position.

In an implementation, the monomer may have a molecular weight of, e.g., about 800 to about 5,000. Within the ranges, a carbon content and solubility in a solvent of the organic layer composition (e.g., a hardmask composition) including the monomer may be optimized.

When the monomer is used as an organic layer material, a uniform thin film may be formed without generation of a pin-hole and a void or degradation of thickness distribution during a bake process, and excellent gap-fill and planarization characteristics may also be obtained when there is a step in a lower substrate (or a layer) or when a pattern is formed.

According to another embodiment, an organic layer composition including the monomer and a solvent may be provided.

The solvent may be a suitable solvent having sufficient solubility or dispersion with respect to the monomer. In an implementation, the solvent may include, e.g., propylene glycol, propylene glycol diacetate, methoxy propanediol, diethylene glycol, diethylene glycol butylether, tri(ethylene glycol)monomethylether, propylene glycol monomethylether, propylene glycol monomethylether acetate, cyclohexanone, ethyllactate, gamma-butyrolactone, N,N-dimethyl formamide, N,N-dimethyl acetamide, methylpyrrolidone, methylpyrrolidinone, acetylacetone, or ethyl 3-ethoxypropionate.

The monomer may be present in the composition in an amount of about 0.1 to about 50 wt %, based on a total weight or amount of the organic layer composition. When the monomer is included in the range, a thickness, surface roughness, and planarization of the organic layer may be controlled.

The organic layer composition may further include a surfactant.

In an implementation, the surfactant may include, e.g., alkylbenzene sulfonate salt, alkyl pyridinium salt, polyethylene glycol, or a quaternary ammonium salt.

The surfactant may be present in the composition in an amount of about 0.001 to about 3 parts by weight, based on 100 parts by weight of the organic layer composition. When the surfactant is included within the range, solubility of a hardmask composition may be secured without changing its optical properties.

According to another embodiment, an organic layer manufactured using the organic layer composition may be provided. The organic layer may be, e.g., formed by coating the organic layer composition on a substrate and heat-treating it for curing and may include, e.g., a hardmask layer, a planarization layer, a sacrificial layer, a filler, and the like for an electronic device.

Hereafter, a method for forming patterns by using the organic layer composition is described.

A method of forming patterns according to one embodiment may include providing a material layer on a substrate, applying the organic layer composition including the monomer and the solvent, heat-treating the organic layer composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

The substrate may be, e.g., a silicon wafer, a glass substrate, or a polymer substrate.

The material layer may be a material to be finally patterned, e.g., a metal layer such as an aluminum layer or a copper layer, a semiconductor layer such as a silicon layer, or an insulation layer such as a silicon oxide layer or a silicon nitride layer. The material layer may be formed through a method such as a chemical vapor deposition (CVD) process.

The organic layer composition may be the same as described above, and may be applied by spin-on coating in a form of a solution. In an implementation, a thickness of the organic layer composition may be, e.g., about 50 Å to about 10,000 Å.

The heat-treating of the organic layer composition may be performed, e.g., at about 100 to about 500° C. for about 10 seconds to about 1 hour.

The silicon-containing thin layer may be formed of, e.g., SiCN, SiOC, SiON, SiOCN, SiC, SiN, and/or the like.

The method may further include forming a bottom anti-reflective coating (BARC) before forming the photoresist layer on the silicon-containing thin layer.

Exposure of the photoresist layer may be performed using, e.g., ArF, KrF, or EUV. After exposure, heat treatment may be performed at about 100° C. to about 500° C.

The etching process of the exposed part of the material layer may be performed through a dry etching process using an etching gas and the etching gas may be, e.g., $CHF_3$, $CF_4$, $Cl_2$, $BCl_3$, and a mixed gas thereof.

The etched material layer may be formed in a plurality of patterns, and the plurality of patterns may include, e.g., a metal pattern, a semiconductor pattern, an insulation pattern, or the like (for example, diverse patterns of a semiconductor integrated circuit device).

Hereinafter, the present disclosure is illustrated in more detail with reference to examples. However, these examples are exemplary, and the present disclosure is not limited thereto.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthesis Example 1

20.6 g (0.1 mol) of terephthaloyl chloride, 47 g (0.2 mol) of 4-methoxypyrene, and 200 g of 1,2-dichloroethane were put in a 3-neck flask and then agitated. Then, 27 g (0.2 mol) of aluminum chloride was little by little added to the solution, and the mixture was slowly heated and reacted at 80° C. for 2 hours. When the reaction was complete, methanol was added thereto, and a precipitate produced therein was filtered, obtaining bis(methoxypyrenylcarbonyl)benzene. Subsequently, 29.7 g (0.05 mol) of bis(methoxypyrenylcarbonyl)benzene and 7.6 g (0.04 mol) of quinoline-3-carbonyl chloride along with 200 g of a chloroform/dichloromethane mixed solution were put in the flask, and the resulting mixture was agitated with a stirring bar and then reacted while 12.5 g (0.05 mol) of aluminum chloride was little by little added thereto. When the reaction was complete, a precipitate obtained by adding methanol thereto was filtered, obtaining a compound. Then, 32.4 g (0.16 mol) of 1-dodecanethiol, 11.2 g (0.2 mol) of potassium hydroxide, and 300 g of N,N-dimethyl formamide were added to the reactant obtained as powder, and the mixture was agitated at 120° C. for 8 hours. The resultant was cooled down to ambient temperature and neutralized by using water and a 10% hydrogen chloride solution, and a compound precipitated therein was washed with flowing water. The obtained compound was dried, tetrahydrofuran was added thereto, 1.9 g (0.05 mol) of lithium aluminum hydride was little by little added thereto, and the mixture was reacted for 12 hours. When the reaction was complete, a reaction byproduct was removed by using a water/methanol mixture, obtaining a compound represented by Chemical Formula 1a.

[Chemical Formula 1a]

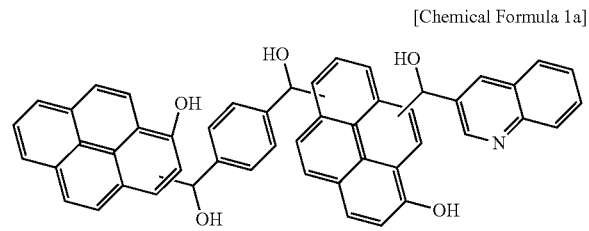

Synthesis Example 2

A compound represented by Chemical Formula 1b was obtained according the same method as Synthesis Example 1 except for using 9.7 g (0.04 mol) of 4,5-dihydrophenanthrene-3-carbonyl chloride instead of 7.6 g (0.04 mol) of quinoline-3-carbonyl chloride.

[Chemical Formula 1b]

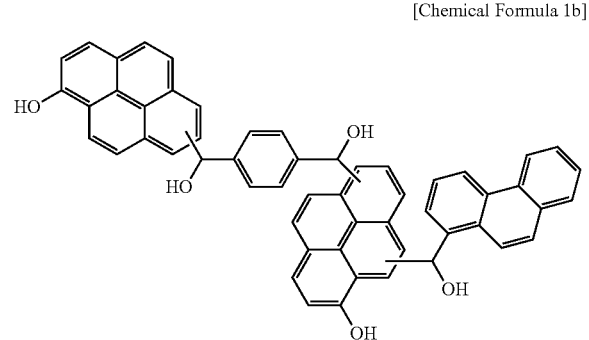

Synthesis Example 3

A compound represented by Chemical Formula 1c was obtained according to the same method as Synthesis Example 1 except for using 20.6 g (0.1 mol) of isophthaloyl chloride instead of 20.6 g (0.1 mol) of the terephthaloyl chloride and 7.8 g (0.04 mol) of 2H-chromene-3-carbonyl chloride instead of 7.6 g (0.04 mol) of the quinoline-3-carbonyl chloride.

[Chemical Formula 1c]

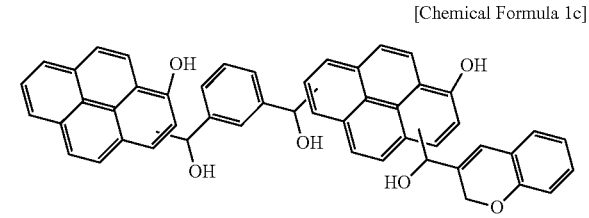

Synthesis Example 4

27.6 g (0.1 mol) of benzoperylene, 41.3 g (0.2 mol) of 5-hydroxy-1-naphthoyl chloride, and 270 g of 1,2-dichloroethane were put in a 3-neck flask and agitated. Then, 27 g (0.2 mol) of aluminum chloride was little by little added to the solution, and the mixture was slowly heated and reacted at 50° C. for 4 hours. When the reaction was complete, methanol was added thereto, and a precipitate produced therein was filtered and dried. Then, 52 g of the dried compound and 28.1 g (0.08 mol) of pyrene-1-carbonylchloride along with 400 g of 1,2-dichloroethane were put in the flask, the mixture was agitated by using a stirring bar, and 40 g (0.3 mol) of aluminum chloride was little by little added thereto. After one hour, 17 g (0.1 mol) of 4-methoxybenzoyl chloride was additionally added thereto at ambient temperature, slowly heated, and reacted at 50° C. for 4 hours. When the reaction was complete, methanol was added thereto, a precipitate produced therein was filtered, subsequently, washed with sufficient methanol, and dried, obtaining a compound. Then, the following reaction was performed according to the same method as Synthesis Example 1, obtaining a compound represented by Chemical Formula 1d.

[Chemical Formula 1d]

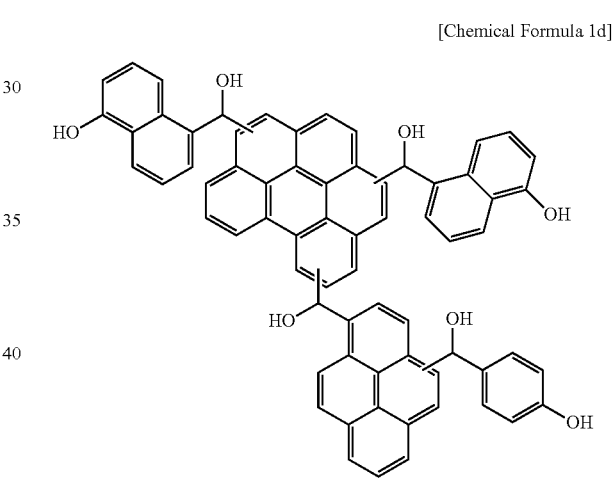

Comparative Synthesis Example 1

41.45 g (0.15 mol) of benzoperylene, 42.2 g (0.3 mol) of benzoylchloride, and 470 g of chloroform/dichloromethane were put in a 3-neck flask. Subsequently, the mixture was agitated by using a stirring bar, 40 g (0.3 mol) of aluminum chloride ($AlCl_3$) was little by little added thereto, and the mixture was heated up to 60° C. and agitated for 8 hours. When the reaction was complete, methanol was added thereto, and a precipitate produced therein was filtered and then, washed with a water/methanol mixed solution to remove a reaction byproduct and non-reacted aluminum chloride. 48.5 g (0.10 mol) of the dried reaction product and 200 g of Raney nickel were agitated with 600 ml of 2-propanol for 1 hour under reflux conditions. When the reaction was complete, the resultant was cooled down to ambient temperature, and subsequently, an organic layer was removed and rotary-evaporated, obtaining a compound represented by Chemical Formula A.

[Chemical Formula A]

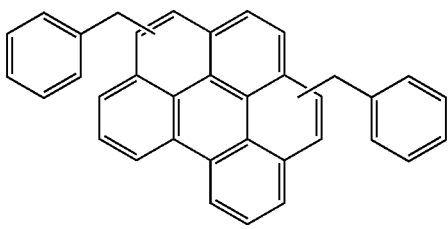

Comparative Synthesis Example 2

20.2 g (0.1 mol) of pyrene, 16.6 g (0.1 mol) of 1,4-bis(methoxymethyl)benzene, and 85 g of PGMEA as a solvent were put in a flask and sufficiently agitated. Subsequently, 1.5 g (0.01 mol) of diethylsulfate was added thereto, and the mixture was heated up to 100° C. and reacted for about 8 hours. When the reaction was complete, a monomer produced therein was removed by using water and methanol, and then, the residue was concentrated, obtaining a compound represented by Chemical Formula B.

[Chemical Formula B]

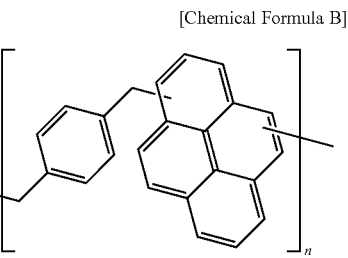

(a weight average molecular weight (Mw)=1,900, polydispersity=1.6, n=6)

Preparation of Hardmask Composition

Example 1

The compound prepared in Synthesis Example 1 was dissolved in 10 g of a mixed solvent of propylene glycolmonoethyl ether acetate (PGMEA) and cyclohexanone (7:3 (v/v)) and filtered, preparing an organic layer composition. The amount of the compound was adjusted in a range of 3 wt % to 13 wt % based on the total weight of the organic layer composition depending on a desired thickness.

Example 2

An organic layer composition was prepared according to the same method as Example 1 except for using the compound of Synthesis Example 2 instead of the compound of Synthesis Example 1.

Example 3

An organic layer composition was prepared according to the same method as Example 1 except for using the compound of Synthesis Example 3 instead of the compound of Synthesis Example 1.

Example 4

An organic layer composition was prepared according to the same method as Example 1 except for using the compound of Synthesis Example 4 instead of the compound of Synthesis Example 1.

Comparative Example 1

An organic layer composition was prepared according to the same method as Example 1 except for using the compound of Comparative Synthesis Example 1 instead of the compound of Synthesis Example 1.

Comparative Example 2

An organic layer composition was prepared according to the same method as Example 1 except for using the compound of Comparative Synthesis Example 2 instead of the compound of Synthesis Example 1.

Evaluation 1: Solubility

The compounds according to Synthesis Examples 1 to 4 and Comparative Synthesis Examples 1 and 2 were respectively put in 100 mL of a propylene glycol monomethylether acetate (PGMEA) solvent at ambient temperature (23° C.±1° C.) until saturated and then, sufficiently agitated, preparing each solution. The solution was filtered, and the obtained solid through the filtering was measured.

The compounds according to Synthesis Examples 1 to 4 and Comparative Synthesis Examples 1 were respectively put in a propylene glycol monomethylether acetate (PGMEA) solvent in a solid content of 10 wt % based on the total weight of a solution, each solution was stored at 5° C., and its stability was evaluated.

The results are provided in Table 1.

TABLE 1

| | Solubility (S) (@ 23° C. ± 1° C.) (S g/100 g PGMEA) | Storage-stability of 10 wt % solution (@ 5° C.) |
|---|---|---|
| Synthesis Example 1 | 43 | Stable for two months or more |
| Synthesis Example 2 | 33 | Stable for two months or more |
| Synthesis Example 3 | 41 | Stable for two months or more |
| Synthesis Example 4 | 36 | Stable for two months or more |
| Comparative Synthesis Example 1 | 10 | Precipitation within 20 days |
| Comparative Synthesis Example 2 | 3 | — |

Referring to Table 1, the compounds according to Synthesis Examples 1 to 4 were dissolved in a relatively greater amount than the compounds having a symmetric structure (according to Comparative Synthesis Examples 1 and 2) and turned out to have excellent solubility.

In addition, the compounds having an asymmetric structure (according to Synthesis Examples 1 to 4) exhibited excellent long-term storage-stability, compared with the compounds having a symmetric structure (according to Comparative Synthesis Examples 1 and 2).

Evaluation 2: Etch Resistance

The organic layer composition according to Examples 1 to 4 and Comparative Example 2 were respectively spin-on coated on a silicon wafer and heat-treated on a hot plate at 400° C. for 90 seconds, forming a 4,000 Å-thick thin film.

Subsequently, the thin film was dry-etched by using N$_2$/O$_2$ mixed gas and CF$_x$ gas for 60 seconds and 100 seconds respectively, and then, the thickness of the thin film was measured again. The thicknesses of the thin film before and after the dry etching and etching time were used to calculate a bulk etch rate (BER) according to the following Calculation Equation 1. The thickness of the thin film was measured by using a thin film thickness meter made by K-MAC.

(Initial thin film thickness−thin film thickness after etching)/etching time (Å/s)  [Calculation Equation 1]

The results are provided in Table 2.

TABLE 2

| | Bulk etch rate (Å/sec) | |
| --- | --- | --- |
| | CHF$_3$/CF$_4$ mixed gas | N$_2$/O$_2$ mixed gas |
| Example 1 | 22.3 | 25.5 |
| Example 2 | 25.4 | 24.5 |
| Example 3 | 26.5 | 24.8 |
| Example 4 | 25.5 | 23.9 |
| Comparative Example 2 | 28.1 | 27.2 |

Referring to Table 2, the thin films respectively formed of the organic layer composition according to Examples 1 to 4 had sufficient etch resistance against etching gas and a low etch rate compared with the thin film formed of the organic layer composition according to Comparative Example 2.

Evaluation 3: Pattern Formation

A 3000 Å-thick silicon oxide (SiO$_x$) layer was formed on a silicon wafer using a chemical vapor deposition (CVD) method. Subsequently, the organic layer composition according to Examples 1 to 4 and Comparative Examples 1 and 2 were respectively spin-coated on the silicon oxide layer and heat-treated at 350° C. for 2 minutes, forming a hardmask layer.

On the hardmask layer, a silicon nitride (SiN$_x$) layer was formed using a chemical vapor deposition (CVD) method. Subsequently, a photoresist for KrF was spin-coated and heat-treated at 110° C. for 60 seconds and then, exposed by using an ASML (XT: 1400, NA 0.93) exposure equipment and developed by using hydroxide tetramethyl ammonium (a 2.38 wt % TMAH aqueous solution).

Then, the patterned photoresist as a mask and a CHF$_3$/CF$_4$ mixed gas plasma were used to dry-etch the silicon nitride (SiN$_x$) layer. The patterned silicon nitride (SiN$_x$) layer through the process as a mask and a N$_2$/O$_2$ mixed gas plasma were used to dry-etch the hardmask layers respectively formed of the hardmask compositions according to Examples 1 to 4 and Comparative Examples 1 to 2. Then, the cross-section of the hardmask patterns was examined by using an electron scanning microscope (SEM).

The patterned hardmask layer was used as a mask and a CHF$_3$/CF$_4$ mixed gas plasma were used to dry-etch the silicon oxide (SiO$_x$) layer, and an organic material remaining on the silicon wafer was all removed by using an oxygen O$_2$ plasma under an ashing condition. Subsequently, the cross-section of the silicon oxide layer pattern was examined by using an electron scanning microscope (SEM).

The results are provided in Table 3.

TABLE 3

| | Cross-section shape of hardmask layer pattern | Cross-section shape of silicon oxide layer pattern |
| --- | --- | --- |
| Example 1 | Vertical shape | Vertical shape |
| Example 2 | Vertical shape | Vertical shape |
| Example 3 | Vertical shape | Vertical shape |
| Example 4 | Vertical shape | Vertical shape |
| Comparative Example 1 | Tapered shape | Tapered shape |
| Comparative Example 2 | Tapered shape | Tapered shape |

Referring to Table 3, the hardmask layers formed of the organic layer compositions according to Examples 1 to 4 and the silicon oxide layers therebeneath were all vertically patterned, while the hardmask layers formed of the organic layer compositions according to Comparative Examples 1 and 2 were not vertically patterned but tapered, e.g., their cross-section became narrower toward the upper end of the pattern.

Accordingly, the organic layer compositions according to Examples 1 to 4 exhibited excellent etching resistance and formed a satisfactory pattern compared with the organic layer composition according to the Comparative Examples, and in addition, a material layer beneath the hardmask layer was also well patterned.

Evaluation 4: Gap-fill Characteristics and Coating Characteristics

The organic layer compositions according to Examples 1 to 4 and Comparative Examples 1 and 2 were respectively coated on a patterned wafer and baked at 350° C. for 2 minutes, and their gap-fill characteristics were examined by using V-SEM equipment.

The gap-fill characteristics were evaluated by examining the pattern cross-section with an electron scanning microscope (SEM) to see whether there was a void, and the coating characteristics were examined with naked eyes and an optical microscope.

TABLE 4

| | Gap-fill characteristics (Void generation) | | Coating properties |
| --- | --- | --- | --- |
| | aspect ratio (1:1.5) | aspect ratio (1:10) | |
| Example 1 | No void | No void | Good |
| Example 2 | No void | No void | Good |
| Example 3 | No void | No void | Good |
| Example 4 | No void | No void | Good |
| Comparative Example 1 | No void | Void | Pin-hole |
| Comparative Example 2 | No void | Void | Pin-hole |

Referring to Table 4, the thin films respectively formed of the organic layer compositions according to Examples 1 to 4 showed no pin-hole on the surface and thus excellent flatness when examined with naked eyes and an optical microscope as well as no void under a deep pattern condition (an aspect ratio 1:10) and thus excellent gap-fill characteristics. The thin films respectively formed of the organic layer compositions according to Comparative Examples 1 to 2 showed a pin-hole on the surface when examined with naked eyes and an optical microscope as well as a void on the patterned wafer and accordingly, relatively insufficient gap-fill characteristics and flatness.

By way of summation and review, a spin-on coating method, instead of a chemical vapor deposition (CVD) method, may be used to form a hardmask layer. The spin-on coating method may not only be easily performed, but may also improve gap-fill characteristics and planarization characteristics. In order to apply the spin-on coating method, a solid in an organic layer material may be soluble in a solvent. However, this solubility may have effects on the etch resistance. Accordingly, an organic layer material may satisfy both properties.

The embodiments may provide a monomer having improved etch resistance and solubility characteristics and thus being applicable to a spin-on coating method.

The embodiments may provide an organic layer having improved etch resistance and planarization characteristics.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A monomer having an asymmetric structure and being represented by one of Chemical Formulae 1-1 and 1-2:

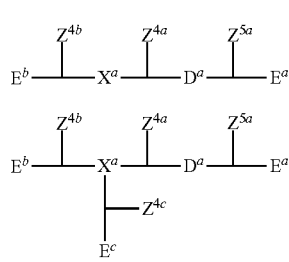

[Chemical Formula 1-1]

[Chemical Formula 1-2]

wherein, in Chemical Formulae 1-1 and 1-2,
$X^a$ is a substituted or unsubstituted aromatic ring group,
$D^a$, $E^a$, $E^b$, and $E^c$ are each independently a substituted or unsubstituted aromatic ring group, or a substituted or unsubstituted heteroaromatic ring group, and
$Z^{4a}$, $Z^{4b}$, $Z^{4c}$, and $Z^{5a}$ are each independently a hydroxy group, a thionyl group, a thiol group, a cyano group, a substituted or unsubstituted amino group, or a halogen atom,
wherein, in Chemical Formula 1-1, at least one of $X^a$, $D^a$, $E^a$, and $E^b$ is a group that includes a hydroxy group, and
wherein, in Chemical Formula 1-2, at least one of $X^a$, $D^a$, $E^a$, $E^b$, and $E^c$ is a group that includes a hydroxy group.

2. The monomer as claimed in claim 1, wherein:
in Chemical Formula 1-1, at least one of $D^a$, $E^a$, and $E^b$ is a substituted or unsubstituted polycyclic aromatic ring group, or a substituted or unsubstituted polycyclic heteroaromatic ring group, or in Chemical Formula 1-1, $X^a$ is a substituted or unsubstituted polycyclic aromatic ring group, and
in Chemical Formula 1-2, at least one of $D^a$, $E^a$, $E^b$, and $E^c$ is a substituted or unsubstituted polycyclic aromatic ring group, or a substituted or unsubstituted polycyclic heteroaromatic ring group, or in Chemical Formula 1-2, $X^a$ is a substituted or unsubstituted polycyclic aromatic ring group.

3. The monomer as claimed in claim 1, wherein, in Chemical Formulae 1-1 and 1-2, $D^a$, $E^a$, $E^b$, and $E^c$ are each independently a substituted or unsubstituted group of one of the following compounds:

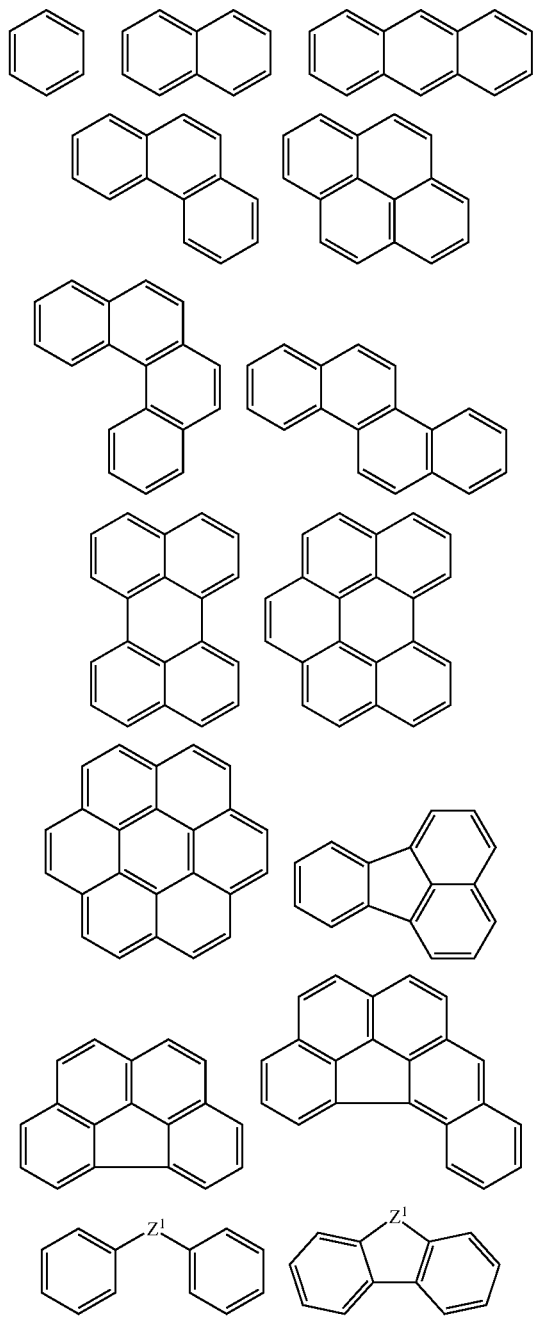

-continued

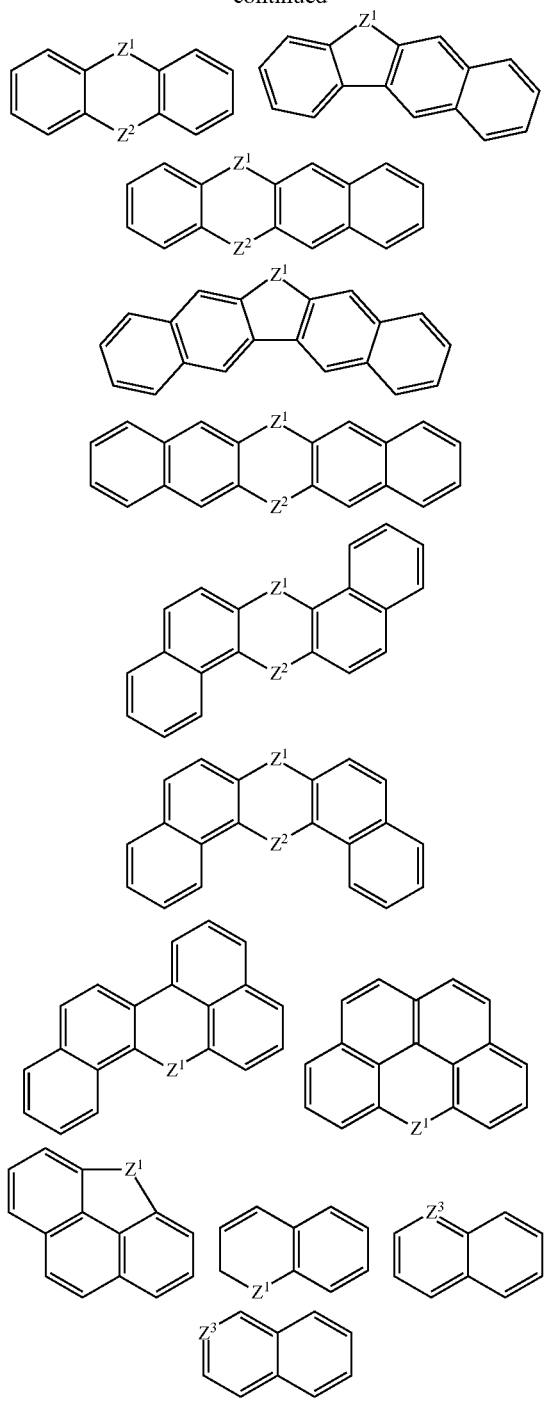

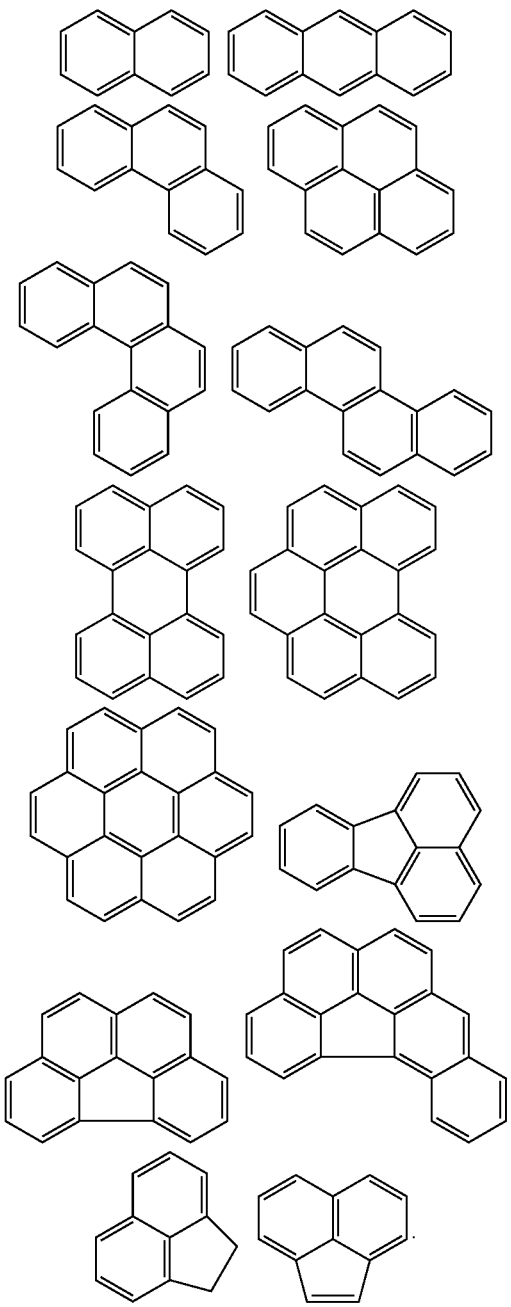

wherein, in the above compounds, $Z^1$ and $Z^2$ are each independently C=O, NR, oxygen (O), or sulfur (S), $Z^3$ is nitrogen (N), or CR, and R is hydrogen, a substituted or unsubstituted C1 to C10 alkyl group, a halogen atom, or a halogen-containing group.

4. The monomer as claimed in claim 3, wherein, in Chemical Formulae 1-1 and 1-2, $X^a$ is a substituted or unsubstituted group of one of the following compounds:

5. The monomer as claimed in claim 1, wherein the monomer has a molecular weight of about 800 to about 5,000.

6. An organic layer composition, comprising:
a solvent; and
a monomer,
wherein the monomer has an asymmetric structure and is represented by one of Chemical Formulae 1-1 and 1-2:

[Chemical Formula 1-1]

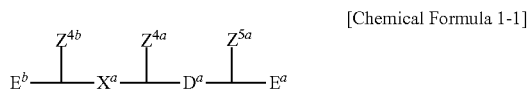

[Chemical Formula 1-2]

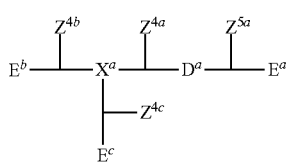

wherein, in Chemical Formulae 1-1 and 1-2, $X^a$ is a substituted or unsubstituted aromatic ring group, $D^a$, $E^a$, $E^b$, and $E^c$ are each independently a substituted or unsubstituted aromatic ring group, or a substituted or unsubstituted heteroaromatic ring group, $Z^{4a}$, $Z^{4b}$, $Z^{4c}$, and $Z^{5a}$ are each independently a hydroxy group, a thionyl group, a thiol group, a cyano group, a substituted or unsubstituted amino group, or a halogen atom, wherein, in Chemical Formula 1-1, at least one of $X^a$, $D^a$, $E^a$, and $E^b$ is a group that includes a hydroxy group, and wherein, in Chemical Formula 1-2, at least one of $X^a$, $D^a$, $E^a$, $E^b$, and $E^c$ is a group that includes a hydroxy group.

7. The organic layer composition as claimed in claim 6, wherein:

in Chemical Formula 1-1, at least one of $D^a$, $E^a$, and $E^b$ is a substituted or unsubstituted polycyclic aromatic ring group, or a substituted or unsubstituted polycyclic heteroaromatic ring group, or in Chemical Formula 1-1, $X^a$ is a substituted or unsubstituted polycyclic aromatic ring group, and in Chemical Formula 1-2, at least one of $D^a$, $E^a$, $E^b$, and $E^c$ is a substituted or unsubstituted polycyclic aromatic ring group, or a substituted or unsubstituted polycyclic heteroaromatic ring group, or in Chemical Formula 1-2, $X^a$ is a substituted or unsubstituted polycyclic aromatic ring group.

8. The organic layer composition as claimed in claim 6, wherein, in Chemical Formulae 1-1 and 1-2, $D^a$, $E^a$, $E^b$, and $E^c$ are each independently a substituted or unsubstituted group of one of the following compounds:

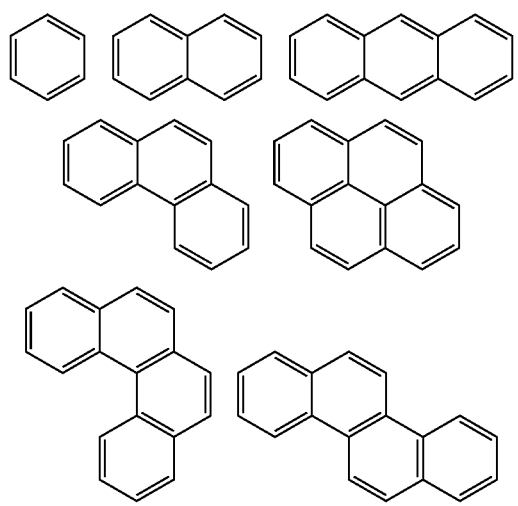

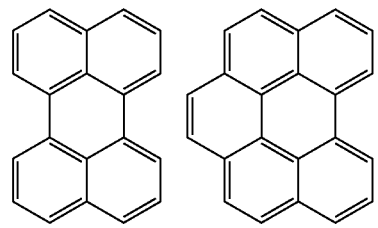

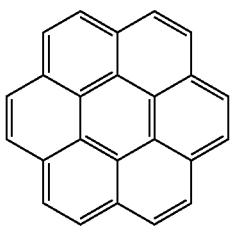
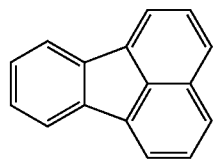

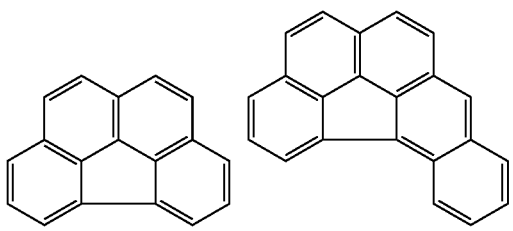

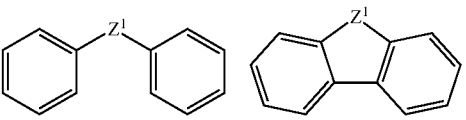

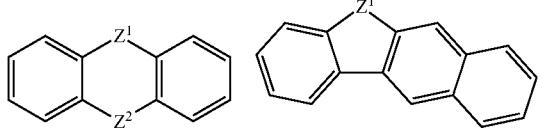

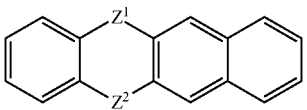

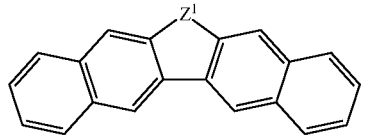

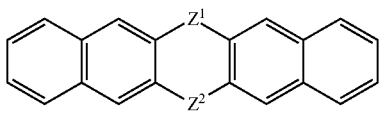

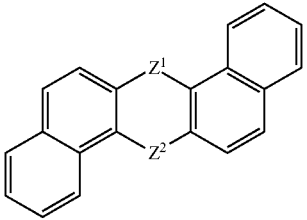

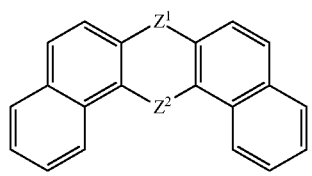

-continued

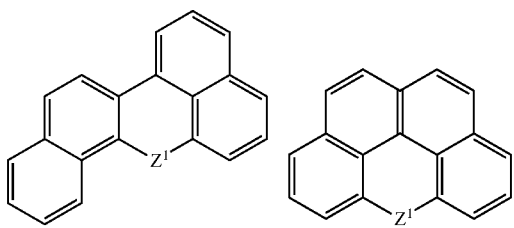

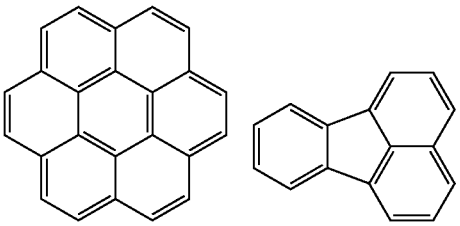

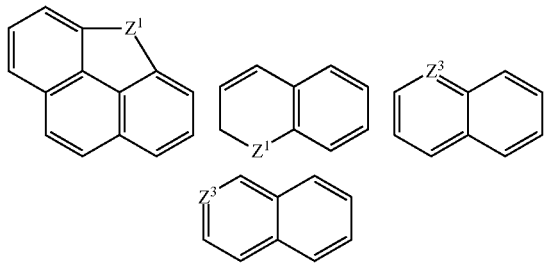

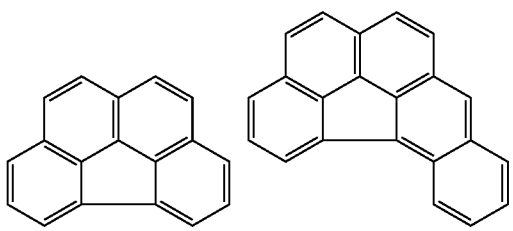

wherein, in the above compounds, $Z^1$ and $Z^2$ are each independently C=O, NR, oxygen (O), or sulfur (S), $Z^3$ is nitrogen (N), or CR, and R is hydrogen, a substituted or unsubstituted C1 to C10 alkyl group, a halogen atom, or a halogen-containing group.

9. The organic layer composition as claimed in claim 8, wherein, in Chemical Formulae 1-1 and 1-2, $X^a$ is a substituted or unsubstituted group of one of the following compounds:

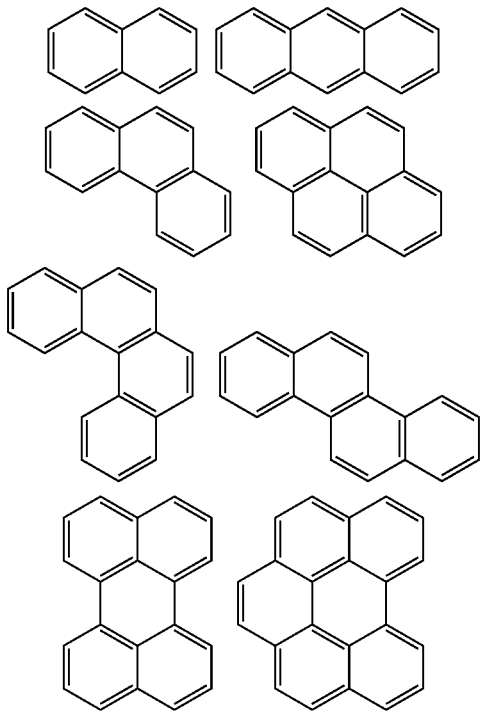

10. The organic layer composition as claimed in claim 6, wherein the monomer has a molecular weight of about 800 to about 5000.

11. A method of forming patterns, the method comprising:
providing a material layer on a substrate,
applying the organic layer composition as claimed in claim 6 on the material layer,
heat-treating the organic layer composition to form a hardmask layer,
forming a silicon-containing thin layer on the hardmask layer,
forming a photoresist layer on the silicon-containing thin layer,
exposing and developing the photoresist layer to form a photoresist pattern,
selectively removing the silicon-containing thin layer and the hardmask layer using the photoresist pattern to expose a part of the material layer, and
etching an exposed part of the material layer.

12. The method as claimed in claim 11, wherein applying the organic layer composition includes performing a spin-on coating method.

13. An organic layer composition, comprising:
a solvent; and
a monomer,
wherein the monomer is represented by one of the following Chemical Formulae 1a to 1d:

Chemical Formula 1a
Chemical Formula 1b
Chemical Formula 1c
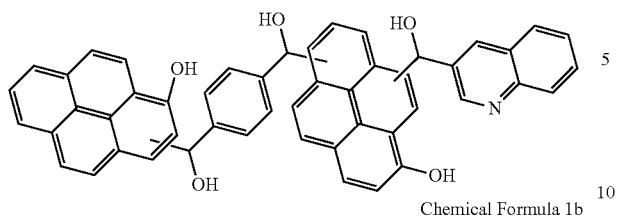
Chemical Formula 1d
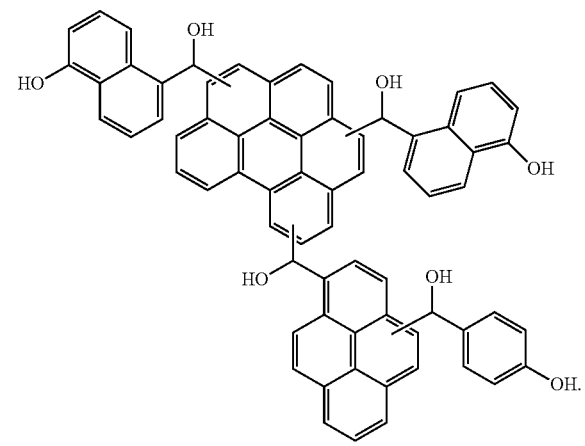
14. A hardmask layer prepared by heat-treating the organic layer composition as claimed in claim 6.
15. A hardmask layer prepared by heat-treating the organic layer composition as claimed in claim 13.
* * * * *